US011285179B2

(12) United States Patent
Tsai et al.

(10) Patent No.: US 11,285,179 B2
(45) Date of Patent: *Mar. 29, 2022

(54) METHOD FOR PREVENTING OR TREATING MOVEMENT DISORDERS WITH LACTIC ACID BACTERIUM

(71) Applicants: BENED BIOMEDICAL CO., LTD., Taipei (TW); ASIAN PROBIOTICS AND PREBIOTICS CORPORATION, Shanghai (CN)

(72) Inventors: Ying-Chieh Tsai, Taipei (TW); Chih-Chieh Hsu, Taipei (TW); Jian-Fu Liao, Taipei (TW); Yun-Fang Cheng, Taipei (TW); Shu-Ting You, Taipei (TW)

(73) Assignees: BENED BIOMEDICAL CO., LTD., Taipei (TW); ASIAN PROBIOTICS AND PREBIOTICS CORPORATION, Shanghai (CN)

( * ) Notice: Subject to any disclaimer, the term of this patent is extended or adjusted under 35 U.S.C. 154(b) by 99 days.

This patent is subject to a terminal disclaimer.

(21) Appl. No.: 16/319,029

(22) PCT Filed: Jul. 19, 2016

(86) PCT No.: PCT/CN2016/090529
§ 371 (c)(1),
(2) Date: Jan. 18, 2019

(87) PCT Pub. No.: WO2018/014225
PCT Pub. Date: Jan. 25, 2018

(65) Prior Publication Data
US 2019/0201461 A1    Jul. 4, 2019

(51) Int. Cl.
*A61K 35/747*      (2015.01)
*A61P 25/14*       (2006.01)
*A23L 33/135*      (2016.01)
*A61P 25/16*       (2006.01)
*A61P 25/02*       (2006.01)
*A61K 35/00*       (2006.01)

(52) U.S. Cl.
CPC .......... *A61K 35/747* (2013.01); *A23L 33/135* (2016.08); *A61P 25/02* (2018.01); *A61P 25/14* (2018.01); *A61P 25/16* (2018.01); *A23V 2002/00* (2013.01); *A23Y 2220/67* (2013.01); *A61K 2035/115* (2013.01)

(58) Field of Classification Search
CPC . A61K 35/747; A61K 2035/115; A61P 25/16; A61P 25/14; A23L 33/135; A23Y 2220/67
See application file for complete search history.

(56) References Cited

U.S. PATENT DOCUMENTS

| 2008/0213271 A1* | 9/2008 | Liu ........................... A61P 3/04 424/139.1 |
| 2015/0306157 A1* | 10/2015 | Tsai ....................... A61P 25/00 424/93.45 |
| 2016/0199425 A1* | 7/2016 | Lue ...................... A61K 38/482 424/93.45 |

FOREIGN PATENT DOCUMENTS

| EP | 2937424 A1 * 10/2015 .............. A61P 25/24 |
| TW | 201540835 A    11/2015 |

OTHER PUBLICATIONS

Wall R., Cryan J.F., Ross R.P., Fitzgerald G.F., Dinan T.G., Stanton C. "Bacterial Neuroactive Compounds Produced by Psychobiotics." Advances in Experimental Medicine and Biology, 2014, vol. 817, pp. 221-239. (Year: 2014).*
Liu et al. Psychotropic Effects of Lactobacillus Plantarum PS128 in Early Life-Stressed and Naive Adult Mice; Brain Research, vol. 1631, pp. 1-12. (Year: 2015).*
Guidone et al. Functional Properties of Lactobacillus Plantarum Strains: A Multivariate Screening Study; LWT-Food Science and Technology, vol. 56, pp. 69-76. (Year: 2013).*
English Abstract Translation of Taiwan Search Report.
US Patent Publication 20150306157 is the counterpart application to Foreign Reference TW 201540835 A.
Liu WH et al., Behav Brain Res. Feb. 1, 2016;298(Pt B):202-9.
English Abstract Translation of Office Action issued by Japan Patent Office for counterpart application 2019-502073 dated Feb. 14, 2020.
Brain Research, Nov. 24, 2015, vol. 1631, pp. 1-12.
Martino, Davide et al., Neuroendocrine Aspects of Tourette Syndrome, International Review of Neurobiology, 2013, vol. 112, pp. 239-279.
Office Action and Search Report dated Feb. 14, 2020 issued by European Patent Office for counterpart application No. 16909155.0.

* cited by examiner

*Primary Examiner* — Susan M Hanley
*Assistant Examiner* — Paul C Martin
(74) *Attorney, Agent, or Firm* — WPAT, P.C., Intellectual Property Attorneys; Anthony King

(57) ABSTRACT

The invention surprisingly found that *Lactobacillus plantarum* subsp. *plantarum* PS128 provides an advantageous effect in treatment or prevention of tic disorders and basal ganglia disorders. Accordingly, the invention provides a method of treating or preventing a movement disorder in a subject, comprising administering to a subject an effective amount of cells of a *Lactobacillus plantarum* subsp. *plantarum* PS128, which is deposited under DSMZ Accession No. DSM 28632.

17 Claims, 12 Drawing Sheets
Specification includes a Sequence Listing.

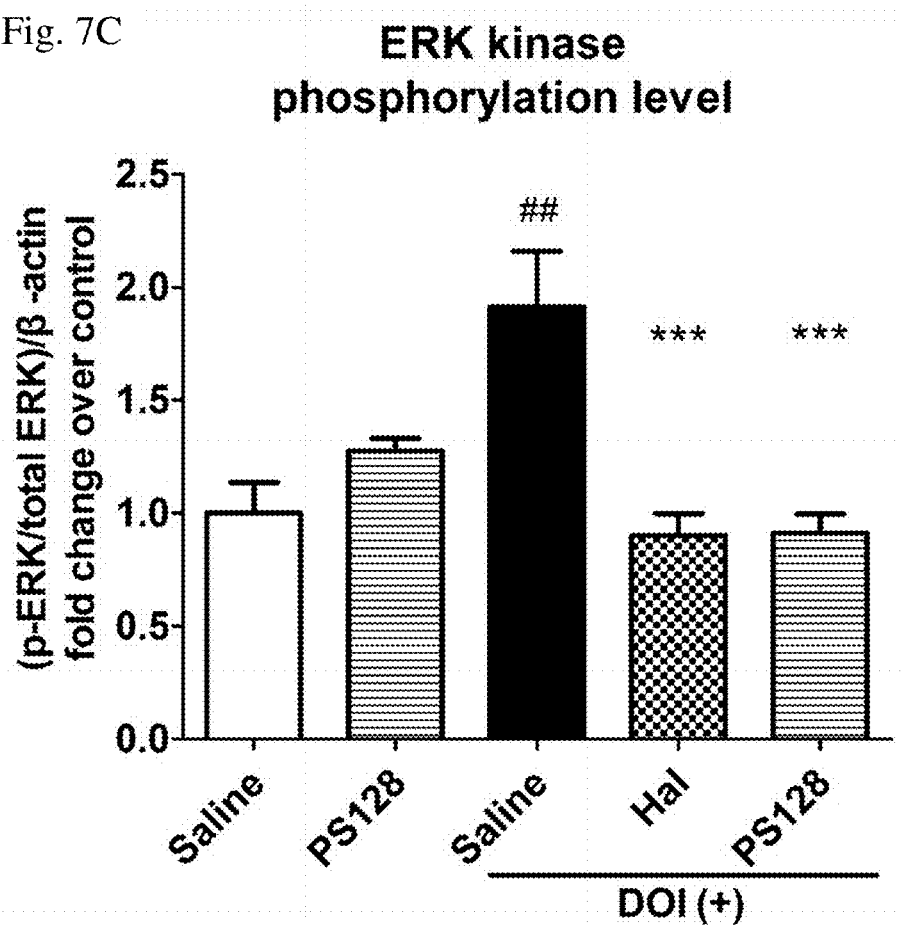

SEQUENCE LISTING

```
<160> NUMBER OF SEQ ID NOS: 5

<210> SEQ ID NO 1
<211> LENGTH: 20
<212> TYPE: DNA
<213> ORGANISM: artificial sequence
<220> FEATURE:
<223> OTHER INFORMATION: primers for PCR amplification of 16S rDNA

<400> SEQUENCE: 1
agagtttgat cmtggctcag                                               20

<210> SEQ ID NO 2
<211> LENGTH: 20
<212> TYPE: DNA
<213> ORGANISM: artificial sequence
<220> FEATURE:
<223> OTHER INFORMATION: primers for PCR amplification of 16S rDNA

<400> SEQUENCE: 2
aaggaggtga tccaaccgca                                               20

<210> SEQ ID NO 3
<211> LENGTH: 1476
<212> TYPE: DNA
<213> ORGANISM: Lactobacillus plantarum subsp. plantarum PS128

<400> SEQUENCE: 3
```

```
ctcaggacga acgctggcgg cgtgcctaat acatgcaagt cgaacgaact ctggtattga      60
ttggtgcttg catcatgatt tacatttgag tgagtggcga actggtgagt aacacgtggg     120
aaacctgccc agaagcgggg gataacacct ggaaacagat gctaataccg cataacaact     180
tggaccgcat ggtccgagyt tgaaagatgg cttcggctat cacttttgga tggtcccgcg     240
gcgtattagc tagatggtgg ggtaacggct caccatggca atgatacgta gccgacctga     300
gagggtaatc ggccacattg ggactgagac acggcccaaa ctcctacggg aggcagcagt     360
agggaatctt ccacaatgga cgaaagtctg atggagcaac gccgcgtgag tgaagaaggg     420
tttcggctcg taaaactctg ttgttaaaga agaacatatc tgagagtaac tgttcaggta     480
ttgacggtat ttaaccagaa agccacggct aactacgtgc cagcagccgc ggtaatacgt     540
aggtggcaag cgttgtccgg atttattggg cgtaaagcga gcgcaggcgg ttttttaagt     600
ctgatgtgaa agccttcggc tcaaccgaag aagtgcatcg gaaactggga aacttgagtg     660
cagaagagga cagtggaact ccatgtgtag cggtgaaatg cgtagatata tggaagaaca     720
ccagtggcga aggcggctgt ctggtctgta actgacgctg aggctcgaaa gtatgggtag     780
caaacaggat tagataccct ggtagtccat accgtaaacg atgaatgcta agtgttggag     840
ggtttccgcc cttcagtgct gcagctaacg cattaagcat tccgcctggg gagtacggcc     900
gcaaggctga aactcaaagg aattgacggg ggcccgcaca agcggtggag catgtggttt     960
aattcgaagc tacgcgaaga accttaccag gtcttgacat actatgcaaa tctaagagat    1020
tagacgttcc cttcggggac atggatacag gtggtgcatg gttgtcgtca gctcgtgtcg    1080
tgagatgttg ggttaagtcc cgcaacgagc gcaaccctta ttatcagttg ccagcattaa    1140
gttgggcact ctggtgagac tgccggtgac aaaccggagg aaggtgggga tgacgtcaaa    1200
tcatcatgcc ccttatgacc tgggctacac acgtgctaca atggatggta caacgagttg    1260
cgaactcgcg agagtaagct aatctcttaa agccattctc agttcggatt gtaggctgca    1320
actcgcctac atgaagtcgg aatcgctagt aatcgcggat cagcatgccg cggtgaatac    1380
gttcccgggc cttgtacaca ccgcccgtca caccatgaga gtttgtaaca cccaaagtcg    1440
gtggggtaac cttttaggaa ccagccgcct aaggtg                              1476

<210> SEQ ID NO 4
<211> LENGTH: 22
<212> TYPE: DNA
<213> ORGANISM: artificial sequence
<220> FEATURE:
<223> OTHER INFORMATION: primers for ERIC-PCR

<400> SEQUENCE: 4
atgtaagctc ctggggattc ac                                               22

<210> SEQ ID NO 5
<211> LENGTH: 22
<212> TYPE: DNA
<213> ORGANISM: artificial sequence
<220> FEATURE:
<223> OTHER INFORMATION: primers for ERIC-PCR

<400> SEQUENCE: 5
aagtaagtga ctggggtgag cg                                               22
```

METHOD FOR PREVENTING OR TREATING MOVEMENT DISORDERS WITH LACTIC ACID BACTERIUM

FIELD OF THE INVENTION

The invention relates to a method for preventing or treating a movement disorder. Particularly, the invention provides a method for preventing or treating tic disorders and basal ganglia disorders by using lactic acid bacterium.

BACKGROUND OF THE INVENTION

The basal ganglia comprise multiple subcortical nuclei, including striatum, *pallidum*, substantia nigra, and subthalamic nucleus, which are situated at the base of the forebrain of vertebrates. The basal ganglia nuclei are strongly interconnected with several other brain areas including cortex, thalamus, and brainstem. Many studies have indicated that it participates in various cerebral functions such as control of voluntary motor movement, procedural learning, routine behavior, eye movement, cognition and emotion. Numerous and diverse neurological conditions are associated with basal ganglia dysfunction behavior control, including hyperkinetic disorders such as hemiballismus (uncontrolled movement on one side of the body caused by damage to the subthalamic nucleus), dystonia (involuntary movement and slowing of intentional movement caused by metabolic, vascular, and structural abnormalities), psychostimulant addiction and Huntington's disease (primarily striatum damage); hyperkinetic disorders such as Parkinson's disease (degeneration of the dopamine—producing cells in the substantia nigra pars compacta); and non-motor disorders such as Tourette syndrome (tics disorders caused by dysfunction of the non-motor loops), obsessive-compulsive disorder (OCD, inability to control either thoughts or actions) (Maya Bronfeld, *Neuroscience and Biobehavioral Reviews* 37 (2013) 1101-1119; Sean C. Godar, *Journal of Neuroscience Methods* 238 (2014) 54-69; J. F. Cheer, *Neuropharmacology* 38 (1999) 533-541; A. M. Ouagazzal, *Neuropsychopharmacology* (2001) Vol. 25, No. 4, 565-575; Toshihide Kuroki, *Brain Research* 972 (2003) 216-221; and Junji Ichikawa, *Brain Research* 698 (1995) 204-208).

Striatum is responsible for selecting which pathway is used. It receives input from the cortex that indicates the required movement and converts this into signals that trigger the direct pathway for the areas of the motor cortex that need to be excited and the indirect pathway for areas that need to be inhibited. Research has identified that the major role of the basal ganglia is to balance excitation and inhibition. The quantity of activity in the motor cortex is adjusted using two distinct pathways: the direct pathway and the indirect pathway. Both pathways run from the cortex through the basal ganglia then back to the motor cortex via the thalamus, although their effects are opposite. The direct pathway causes the thalamus to send excitatory signals back to the motor cortex and so increases activity. The muscles controlled by the parts of the motor cortex receiving signals from the direct pathway become more active, causing the muscles to contract, thereby reinforcing the desired movement. The indirect pathway causes the thalamus to send inhibitory signals to the motor cortex and so suppresses activity. The muscles controlled by areas of the motor cortex receiving inhibitory signals relax, preventing muscle action that would interfere with the movement.

Gilles de la Tourette syndrome (GTS), also called Tourette syndrome (TS) or Tourette's disorder, is an inherited neurological disorder onset in childhood which often coexists with or is complicated by OCD & ADHD. TS patients are characterized by the presence of multiple motor tics and at least one phonic tic. Tics are sudden, repetitive, nonrhythmic motor movements (motor tics) or vocalizations (phonic tics) involving discrete muscle groups. Although the exact causes of TS are unknown, many studies indicate that tics result from dysfunction in the thalamus, basal ganglia, and frontal cortex of the brain involving abnormal activity of brain chemicals or neurotransmitters like dopamine.

Parkinson's disease occurs when nerve cells, or neurons, in an area of the brain that controls movement become impaired and/or die. Normally, these neurons produce an important brain chemical known as dopamine, but when the neurons die or become impaired, they produce less dopamine. This shortage of dopamine causes the movement problems of people with Parkinson's.

Lactic acid bacteria (LAB) is a group of Gram-positive bacteria generally used in the production of fermented foods. The benefits of LAB in dietary and clinical applications have been widely studied. However, the effectiveness of LAB varies by strain. Many studies have shown that production and manufacturing methods and the food carrier may influence the properties of probiotic strains, and have an impact on the outcome of clinical intervention studies. Recent studies have revealed that gut microbiota communicates with the central nerve system (CNS) through different pathways (neural, immune and endocrine) and introduced the idea of the gut-brain-axis (GBA). Certain LAB strains, also called "psychobiotics," influence the brain function and ameliorate behavioral changes through GBA. *Lactobacillus helveticus* ROO52 has been shown to reduce anxiety-like behaviors in rodents (Ohland C L, Kish L, Bell H, Thiesen A, Hotte N, Pankiv E, Madsen K L (2013) *Effects of Lactobacillus helveticus on murine behavior are dependent on diet and genotype and correlate with alterations in the gut microbiome. Psychoneuroendocrinology* 38:1738-1747). *Lactobacillus rhamnosus* JB-1 can reduce stress-induced corticosterone and anxiety- and depression-related behavior and central GABA receptor expression in a mouse via the vagus nerve (Bravo J A, Forsythe P, Chew M V, Escaravage E, Savignac H M, Dinan T G, Bienenstock J, Cryan J F (2011) *Ingestion of Lactobacillus strain regulates emotional behavior and central GABA receptor expression in a mouse via the vagus nerve. Proc Natl Acad Sci USA* 108:16050-16055). Heat-killed *Lactobacillus brevis* SBC8803 increases both efferent gastric vagal nerve activity and afferent intestinal vagal nerve activity in rats. *Lactobacillus reuteri* might affect pain perception through targeting an ion channel in enteric sensory nerves (Horii Y, Nakakita Y, Misonou Y, Nakamura T, Nagai K (2015) *The serotonin receptor mediates changes in autonomic neurotransmission and gastrointestinal transit induced by heat-killed Lactobacillus brevis SBC*8803. *Benef Microbes*. 6(6): 817-22).

*Bifidobacterium infantis* 35624 has been shown to reduce plasma corticosterone concentrations and visceral pain in rat model (McKernan D P, Fitzgerald P, Dinan T G, Cryan J F. (2010) *The probiotic Bifidobacterium infantis 35624 displays visceral antinociceptive effects in the rat. Neurogastroenterol Motil*. 22(9):1029-35, e268). *Bifidobacterium longum* 1714 reduces stress, anxiety and depression-related behaviours whereas *Bifidobacterium breve* 1205 reduces general anxiety behaviors and induces weight loss (Savignac H M, Kiely B, Dinan T G, Cryan J F. (2014) *Bifidobacteria exert strain-specific effects on stress-related behavior and physiology in BALB/c mice. Neurogastroenterol Motil*. November; 26(11): 1615-27. doi: 10.1111/nmo.12427).

Depression can be caused by a lack of the neurotranmitter serotonin in the brain. The other reason for depression is caused by a lack of the dopamine in the brain. However, Parkinson's disease involves nerve cells or neurons impair and/or die and TS involves dopamine dysfunction such as dopamine excess or supersensitivity of the postsynaptic dopamine receptors. Obviously, the cause and mechanism of depression are different from those of TS and Parkinson's disease, so treatment, prevention and/or inhibition of TS and Parkinson's disease cannot be derived from those of depression.

As shown above, different *Bifidobacterium* strains exhibit various functions and beneficial effects in treatment or prevention of diseases or disorders, so there is a need to explore new functions of the *Bifidobacterium* strain.

SUMMARY OF THE INVENTION

The invention identifies that *Lactobacillus plantarum* subsp. *plantarum* PS128 (hereinafter sometimes referred to as PS128) shows an effect in treating or preventing a movement disorder. Accordingly, the invention provides a method of treating or preventing a movement disorder in a subject, comprising administering to a subject an effective amount of cells of a *Lactobacillus plantarum* subsp. *plantarum* PS128, which is deposited under DSMZ Accession No. DSM 28632. The invention also provides a use of a *Lactobacillus plantarum* subsp. *plantarum* PS128, which is deposited under DSMZ Accession No. DSM 28632, in the manufacture of a preparation for treating or preventing a movement disorder in a subject. In some embodiments, the preparation is a medicament, health food or a food.

In one embodiment, PS128 has the 16S rDNA sequence as set forth in SEQ ID NO:3. In one embodiment, PS128 can be used in the form of whole bacteria which may be living or dead. In one embodiment, PS 128 is prepared as a composition or mixture.

In some embodiments, the movement disorder includes, but is not limited to, a basal ganglia disorder, an essential tremor, a Lewy body disease, hypokinetic disease, various types of peripheral neuropathy, dystonia, hypokinesia (including akinesia), dyskinesia, and tic disorder.

DETAILED DESCRIPTION OF THE INVENTION

Figure 1:
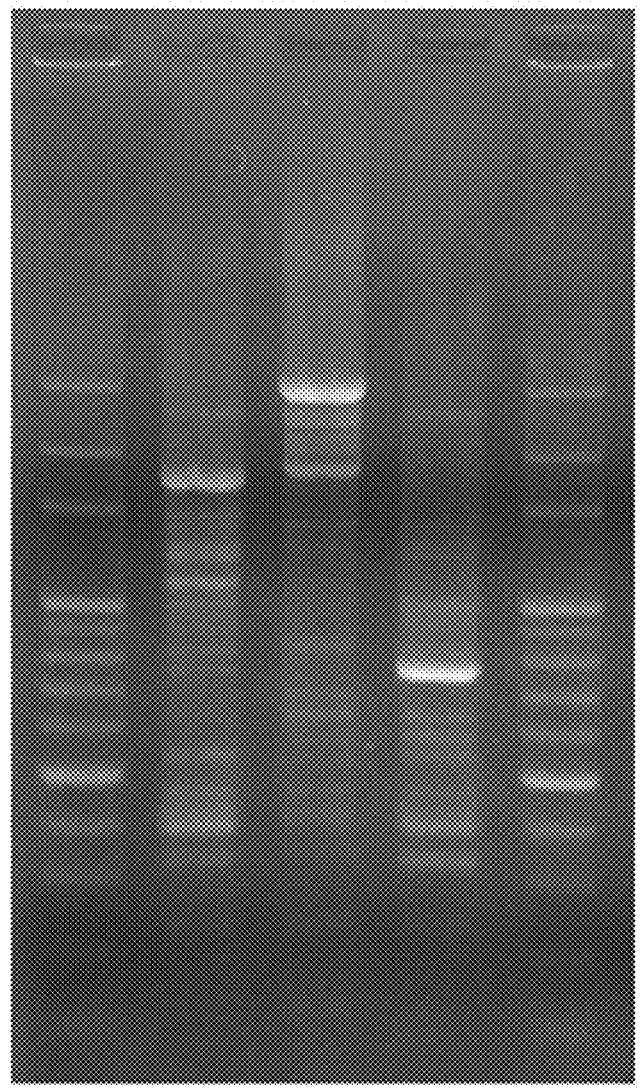
FIG. 1 shows an electrophoresis photograph showing the ERIC-PCR profiles of *Lactobacillus plantarum* strains, wherein M represents DNA ladder; ATCC 14917$^T$ represents *Lactobacillus plantarum* subsp. *plantarum*; and BCRC 17638$^T$ represents *Lactobacillus plantarum* subsp. *argentoratensis*.

The invention surprisingly found that *Lactobacillus plantarum* subsp. *plantarum* PS128 provides an advantageous effect in treatment or prevention of movement disorders, particularly, tic disorders and basal ganglia disorders.

Terms not specifically defined herein should be understood according to the meaning that would be given to them by one of skill in the art in light of the disclosure and the context. As used in the specification, however, unless specified to the contrary, the following terms have the meaning indicated according to the following conventions.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

As used herein, the terms "a," "an," and "the" are to be understood as meaning both singular and plural, unless explicitly stated otherwise. Thus, "a," "an," and "the" (and grammatical variations thereof where appropriate) refer to one or more.

As used herein, the term "disorder" is used interchangeably with "disease" or "condition."

The term "treatment" is understood as meaning to lessen or decrease at least one sign, symptom, indication, or effect of a specific disease or condition. As used herein, "prevention" is understood as to limit, reduce the rate or degree of onset, or inhibit the development of at least one sign or symptom of a disease or condition.

The term "probiotic" is recognized in the state of the art as a microorganism which, when administered in adequate amounts, confers a health benefit to the host. A probiotic microorganism must fulfil several requirements related to lack of toxicity, viability, adhesion and beneficial effects. These probiotic features are strain-dependent, even among bacteria of the same species.

The term "pharmaceutically acceptable" as used herein refers to compounds, materials, compositions, and/or dosage forms which are, within the scope of sound medical judgment, suitable for use in contact with the tissues of a subject (either a human or non-human animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The term "edible carrier" refers to compounds, materials, compositions, and/or dosage forms which are suitable for use in contact with the tissues of a subject. Each carrier must also be "acceptable" in the sense of being compatible with the other ingredients of the formulation.

The term "effective amount" as used herein is the amount of colony forming units (cfu) for each strain in the composition that is high enough to significantly modify the condition to be treated in a positive way but low enough to avoid serious side effects (at a reasonable benefit/risk ratio), within the scope of sound medical judgment.

In one aspect, the invention provides a method of treating or preventing a movement disorder in a subject, comprising administering to a subject an effective amount of cells of a *Lactobacillus plantarum* subsp. *plantarum* PS128, which is deposited under DSMZ Accession No. DSM 28632. The invention also provides a use of a *Lactobacillus plantarum* subsp. *plantarum* PS128, which is deposited under DSMZ Accession No. DSM 28632, in the manufacture of a preparation for treating or preventing a movement disorder in a subject. The invention also provides a *Lactobacillus plantarum* subsp. *plantarum* PS128, which is deposited under DSMZ Accession No. DSM 28632, for treating or preventing a movement disorder in a subject. In some embodiments, the preparation is a medicament, health food or a food.

In one embodiment, *Lactobacillus plantarum* subsp. *plantarum* PS128 has the 16S rDNA sequence as set forth in SEQ ID NO:3.

In one embodiment, PS128 can be used in the form of whole bacteria which may be living or dead. Preferably the bacterial cells are present as living, viable cells. In one embodiment, PS128 can be partial cells of bacteria or a cell mixture of viable cells and dead partial or whole cells.

In one embodiment, PS 128 is prepared as a composition or mixture.

The movement disorder includes, but is not limited to, a basal ganglia disorder, an essential tremor, a Lewy body disease, hypokinetic disease, various types of peripheral neuropathy, dystonia, hypokinesia (including akinesia), dyskinesia, and tic disorder.

In one embodiment, basal ganglia disorders refer to a group of physical dysfunctions that occur when the group of nuclei in the brain known as the basal ganglia fail to properly suppress unwanted movements or to properly prime upper motor neuron circuits to initiate motor function. Increased output of the basal ganglia inhibits thalamocortical projection neurons. Proper activation or deactivation of these neurons is an integral component for proper movement. If something causes too much basal ganglia output, then the thalamocortical projection neurons become too inhibited and one cannot initiate voluntary movement. These disorders are known as hypokinetic disorders. However, a disorder leading to abnormally low output of the basal ganglia leads to a relative lack of inhibition of the thalamocortical projection neurons. This situation leads to an inability to suppress unwanted movements. These disorders are known as hyperkinetic disorders. In some embodiments, the basal ganglia disorder includes but is not limited to hemiballismus (uncontrolled movement on one side of the body caused by damage to the subthalamic nucleus), dystonia (involuntary movement and the slowing of intentional movement caused by metabolic, vascular, and structural abnormalities), psychostimulant addiction, Huntington's disease (primarily striatum damage), Parkinson's disease (degeneration of the dopamine-producing cells in the substantia nigra pars compacta), Tourette syndrome (tics disorders caused by dysfunction of the non-motor loops) and obsessive-compulsive disorder (OCD, inability to control either thoughts or actions).

In one embodiment, the motor symptom is Parkinson's disease, MPTP-induced motor deficit, slowness and difficulty of movement, or chronic motor disorder.

In one embodiment, the tic disorder is Tourette syndrome, DOI-induced tic-linked disorder, chronic motor disorder, or vocal tic disorder.

In an embodiment, PS128 shows a protection of dopaminergic system in host's CNS. In a further embodiment, PS128 rescues the MPTP-induced dopaminergic cells degeneration and increases tyrosine hydroxylase (TH) expression level.

In an embodiment, PS128 shows a modulation of dopamine neurotransmission in basal ganglia. In a further embodiment, DOI induced prefrontal cortical dopamine increases, while PS128 administration modulates this tendency and significantly increases dopamine metabolites total level and dopamine turnover ratio in prefrontal cortex. Preferably, the neurotransmitter is selected from the group consisting of dopamine (DA), dihydroxyphenylacetic acid (DC), and homo-vanillic acid (HVA).

In another further embodiment, PS128 increases dopamine transporter expression level in prefrontal cortex and striatum. Moreover, after the administration of PS128, the dopamine downstream signaling (extracellular signal-regulated kinases, ERK; dopamine and cAMP regulated phosphoprotein, DARPP) activations were increased in rat striatum and prefrontal cortex while dopamine downstream signaling was significantly attenuated during DOI treatment.

In another further embodiment, PS128 shows the ability as a dopamine signaling stabilizer (DSS) that could improve motor disorders and show neuroprotective effects for host's CNS. PS128 could modulate DA transmission and regulates both hyper- and hypoactive functioning depending on the prevailing dopaminergic tone.

The cells of P128 can be prepared as a composition or mixture in any form suitable for administration, in particular oral administration. This includes, for instance, solids, semi-solids, liquids, and powders.

The amount of PS128 cells for administration is at least $10^6$ colony forming unit (cfu) per day, of the strains of PS128 as mentioned above: at least $10^7$ cfu per day, $10^8$ cfu per day or $10^9$ cfu per day, of the strains of PS128 as mentioned above.

Preferably, the amount of PS128 cells for administration ranges from $10^6$ to $10^{14}$, $10^7$ to $10^{14}$, $10^8$ to $10^{14}$, $10^9$ to $10^{14}$, $10^{10}$ to $10^{14}$, $10^{11}$ to $10^{14}$, $10^{12}$ to $10^{14}$, $10^{12}$ to $10^{14}$, $10^{13}$ to $10^{14}$, $10^6$ to $10^{13}$, $10^6$ to $10^{12}$, $10^6$ to $10^{11}$, $10^6$ to $10^{10}$, $10^6$ to $10^9$, $10^6$ to $10^8$, $10^6$ to $10^7$, $10^7$ to $10^{13}$, $10^7$ to $10^{12}$, $10^7$ to $10^{11}$, $10^7$ to $10^{10}$, $10^7$ to $10^9$, $10^7$ to $10^8$, $10^8$ to $10^{13}$, $10^8$ to $10^{12}$, $10^8$ to $10^{11}$, $10^8$ to $10^{10}$, $10^8$ to $10^9$, $10^9$ to $10^{13}$, $10^9$ to $10^{12}$, $10^9$ to $10^{11}$, or $10^9$ to $10^{10}$ cfu per day.

Examples of the PS128 composition or mixture include nutritional compositions or mixtures, including food products and in particular dairy products.

The composition or mixture can be, for example, a capsule, tablet, drink, powder or dairy product. Optionally, other strains of LAB may be present. Preferably the present nutritional composition or mixture is a baby food, an infant milk formula or an infant follow-on formula. Preferably the present composition or mixture is a nutraceutical or a pharmaceutical product, a food product, a health food, a nutritional supplement or medical food.

Nutritional compositions or mixtures of the invention also include food supplements, and functional food. A "food supplement" designates a product made from compounds usually used in foodstuffs, but which is in the form of tablets, powder, capsules, portion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

If the composition or mixture according to the invention is a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, lozenges, granules, powders, suspensions, sachets, pastilles, sweets, bars, syrups and corresponding administration forms, usually in the form of a unit dose. Preferably, the dietary supplement comprising the composition or mixture of the invention is administered in the form of tablets, lozenges, capsules or powders, manufactured in conventional processes of preparing dietary supplements.

The present invention is described in greater detail by the examples presented below, which are preceded by a brief description of the figures. It goes without saying, however, that these examples are given by way of illustration of the subject of the invention and do not constitute in any manner a limitation thereto. The percentages are given by weight unless otherwise stated.

EXAMPLES

Example 1 Isolation and Genetic Typing of Lactobacillus Plantarum Subsp. Plantarum PS128

Lactobacillus plantarum subsp. plantarum PS128 (hereinafter referred to as PS128) was isolated from fu-tsai, traditional fermented mustard products of Taiwan, and was cultured in specific artificial culture medium. 16S rRNA gene from PS128 (SEQ ID NO. 3) was analyzed by direct sequencing of about 1000 nucleotides of PCR-amplified 16S rDNA wherein the primers represented by SEQ ID NO: 1 and SEQ ID NO: 2 were used. Genomic DNA extraction, PCR mediated amplification of the 16S rDNA, purification of the PCR product, and sequencing of the purified PCR product were carried out under the condition indicated in Table 1.

The resulting sequence was put into the alignment software provided online by the National Center for Biotechnology Information (NCBI), aligned manually and compared with representative 16S rDNA sequences of organisms belonging to the Firmicutes. For comparison, 16S rDNA sequences were also obtained from the database provided online by the NCBI. As a result of this analysis, the following Table 2 lists those organisms whose 16S rDNA sequences show the highest similarity values compared to the 16S rDNA sequence of Lactobacillus plantarum subsp. plantarum PS128.

TABLE 1

| Composition of the PCR reaction solution (25 µl per PCR tube) | |
|---|---|
| 8F: (5'-AGAGTTTGATCMTGGCTCAG-3') | (SEQ ID NO: 1) |
| 15R: (5'-AAGGAGGTGATCCAACCGCA-3') | (SEQ ID NO: 2) |
| Component | Volume |
| Template DNA (10 ng/µl) | 1 µl |
| 10× PCR buffer | 2.5 µl |
| dNTP (2.5 mM) | 2 µl |
| Forward primer (10 µM) | 0.5 µl |
| Reverse primer (10 µM) | 0.5 µl |

TABLE 1-continued

| | |
|---|---|
| TaKaRa Ex Taq HS | 0.125 µl |
| Molecular biology grade water | 18.375 µl |
| Total volume | 25 µl |

PCR condition: 98° C. 2.5 min.; 15 cycles (98° C. 15 sec.; 50° C. 30 sec.; 72° C. 20 sec.); 72° C. 5 min.; 4° C., ∞.

TABLE 2

Comparison Between 16S rDNA Sequences

| Strain (GenBank accession number) | 16S rRNA gene sequence similarity to PS128 (%) |
|---|---|
| Lactobacillus plantarum subsp. plantarum ST-III (NC_014554.1) | 99.8% |
| Lactobacillus plantarum subsp. plantarum P-8 (NC_021224.2) | 99.7% |
| Lactobacillus plantarum 16 (NC_021514.1) | 99.7% |
| Lactobacillus brevis ATCC 367 (NC_008497.1) | 93.8% |
| Lactobacillus rhamnosus ATCC 8530 (NC_017491.1) | 92.4% |
| Lactobacillus reuteri DSM 20016 (NC_009513.1) | 90.5% |
| Lactobacillus gasseri ATCC 33323 (NC_008530.1) | 90.0% |

The partial 16S rDNA sequence of PS128 shows highest similarity to Lactobacillus plantarum subsp. plantarum. Consequently, PS128 represents a strain of Lactobacillus plantarum subsp. plantarum, but also represents a new species within the genus Lactobacillus.

Lactobacillus plantarum subsp. plantarum PS128 was deposited under Budapest Treaty at Leibniz Institute DSMZ-German Collection of Microorganisms and Cell Cultures (Inhoffenstr. 7 B, D-38124 Braunschweig, Germany) on Mar. 31, 2014 and has been given the DSMZ Accession No. DSM 28632 by the International Depositary Authority. This biological material was subjected to viability testing and passed.

```
Lactobacillus plantarum subsp. plantarum PS128
16S rDNA sequence
                                        (SEQ ID NO: 3)
CTCAGGACGAACGCTGGCGGCGTGCCTAATACATGCAAGTCGAACGAAC

TCTGGTATTGATTGGTGCTTGCATCATGATTTACATTTGAGTGAGTGGC

GAACTGGTGAGTAACACGTGGGAAACCTGCCCAGAAGCGGGGGATAACA

CCTGGAAACAGATGCTAATACCGCATAACAACTTGGACCGCATGGTCCG

AGYTTGAAAGATGGCTTCGGCTATCACTTTTGGATGGTCCCGCGGCGTA

TTAGCTAGATGGTGGGGTAACGGCTCACCATGGCAATGATACGTAGCCG

ACCTGAGAGGGTAATCGGCCACATTGGGACTGAGACACGGCCCAAACTC

CTACGGGAGGCAGCAGTAGGGAATCTTCCACAATGGACGAAAGTCTGAT

GGAGCAACGCCGCGTGAGTGAAGAAGGGTTTCGGCTCGTAAAACTCTGT

TGTTAAAGAAGAACATATCTGAGAGTAACTGTTCAGGTATTGACGGTAT

TTAACCAGAAAGCCACGGCTAACTACGTGCCAGCAGCCGCGGTAATACG

TAGGTGGCAAGCGTTGTCCGGATTTATTGGGCGTAAAGCGAGCGCAGGC

GGTTTTTTAAGTCTGATGTGAAAGCCTTCGGCTCAACCGAAGAAGTGCA

TCGGAAACTGGGAAACTTGAGTGCAGAAGAGGACAGTGGAACTCCATGT

GTAGCGGTGAAATGCGTAGATATATGGAAGAACACCAGTGGCGAAGGCG

GCTGTCTGGTCTGTAACTGACGCTGAGGCTCGAAAGTATGGGTAGCAAA
```

-continued

CAGGATTAGATACCCTGGTAGTCCATACCGTAAACGATGAATGCTAAGT

GTTGGAGGGTTTCCGCCCTTCAGTGCTGCAGCTAACGCATTAAGCATTC

CGCCTGGGGAGTACGGCCGCAAGGCTGAAACTCAAAGGAATTGACGGGG

GCCCGCACAAGCGGTGGAGCATGTGGTTTAATTCGAAGCTACGCGAAGA

ACCTTACCAGGTCTTGACATACTATGCAAATCTAAGAGATTAGACGTTC

CCTTCGGGGACATGGATACAGGTGGTGCATGGTTGTCGTCAGCTCGTGT

CGTGAGATGTTGGGTTAAGTCCCGCAACGAGCGCAACCCTTATTATCAG

TTGCCAGCATTAAGTTGGGCACTCTGGTGAGACTGCCGGTGACAAACCG

GAGGAAGGTGGGGATGACGTCAAATCATCATGCCCCTTATGACCTGGGC

TACACACGTGCTACAATGGATGGTACAACGAGTTGCGAACTCGCGAGAG

TAAGCTAATCTCTTAAAGCCATTCTCAGTTCGGATTGTAGGCTGCAACT

CGCCTACATGAAGTCGGAATCGCTAGTAATCGCGGATCAGCATGCCGCG

GTGAATACGTTCCCGGGCCTTGTACACACCGCCCGTCACACCATGAGAG

TTTGTAACACCCAAAGTCGGTGGGGTAACCTTTTAGGAACCAGCCGCCT

AAGGTG

Example 2 Identification of Novel Bacterial Strains of *Lactobacillus Plantarum* Subsp. *Plantarum* PS128 Using ERIC-PCR Profiles ERIC-PCR was conducted to further distinguish the subspecies of bacteria with high sequence similarity. The ERIC-PCR profile of *Lactobacillus plantarum* strains was carried out under the condition indicated in Table 3. DNA extracted from PS128 and two *Lactobacillus plantarum* strains were used as templates. The obtained amplification products were electrophoresed and the patterns were compared as shown in FIG. 1, wherein the primers represented by SEQ ID NO: 4 and SEQ ID NO: 5 were used.

```
ERIC1R:
                                     (SEQ ID NO: 4)
(5'-ATGTAAGCTCCTGGGGATTCAC-3')

ERIC2F:
                                     (SEQ ID NO: 5)
(5'-AAGTAAGTGACTGGGGTGAGCG-3')
```

TABLE 3

Composition of the PCR reaction solution (25 μl per PCR tube)

| Component | Volume |
| --- | --- |
| ddH$_2$O | 16.3 μl |
| 10X PCR buffer | 2.5 μl |
| dNTP | 2.0 μl |
| MgCl$_2$ (25 mM) | 1.0 μl |
| primer (GTG)$_5$ (10 μM) | 2.0 μl |
| rTaq polymerase | 0.2 μl |
| DNA template (10 μM) | 1.0 μl |

PCR Conditions: 94° C., 5 min.; 35 cycles (94° C., 30 sec.; 45° C., 1 min.; 65° C., 6 min.); 65° C., 6 min.; 4° C., ∞.

As shown in FIG. 1, Lane M represents DNA ladder (250-10000 bp); ATCC 14917$^T$ represents *Lactobacillus plantarum* subsp. *plantarum*; and BCRC 17638$^T$ represents *Lactobacillus plantarum* subsp. *argentoratensis*.

As indicated by white arrows, the bands of PS128 are unique in position among those of ATCC 14917$^T$ or BCRC 17638$^T$ and hence the result in FIG. 1 shows that even though PS128 and ATCC 14917$^T$ all belong to *Lactobacillus plantarum* subsp. *plantarum*, they are still different bacterial strains. Consequently, PS128 represents a new strain of *Lactobacillus plantarum* subsp. *plantarum*.

Example 3 Analytical Profile Index (API) Typing

Sugar utilization for PS128 used in the present invention was investigated using API 50 CHL kit (bioMerieux, France), and the results are shown in Table 4. The fermentation test indicates that PS128 harbors a biochemical property similar to *Lactobacillus plantarum* subsp. *plantarum*.

TABLE 4

Results of Fermentation Test$^a$

| Carbohydrates Substrate Strips | PS128 |
| --- | --- |
| CONTROL | − |
| Glycerol | − |
| Erythritol | − |
| D-Arabinose | − |
| L-Arabinose | + |
| D-Ribose | + |
| D-Xylose | + |
| L-Xylose | − |
| D-Adonitol | − |
| Methyl-β-D-Xylopyranoside | − |
| D-Galactose | + |
| D-Glucose | + |
| D-Fructose | + |
| D-Mannose | + |
| L-Sorbose | − |
| L-Rhamnose | + |
| Dulcitol | − |
| Inositol | − |
| D-Mannitol | + |
| D-Sorbitol | + |
| Methyl-α-D-mannopyranoside | + |
| Methyl-α-D-glucopyranoside | − |
| N-Acetyl glucosamine | + |
| Amygdalin | + |
| Arbutin | + |
| Esculin ferric citrate | + |
| Salicin | + |
| D-Cellobiose | + |
| D-Maltose | + |
| D-Lactose (bovine origin) | + |
| D-Melibiose | + |
| D-Saccharose (sucrose) | + |
| D-Trehalose | + |
| Inulin | + |
| D-Melezitose | + |
| D-Raffinose | + |
| Amidon (starch) | − |
| Glycogen | − |
| Xylitol | − |
| Gentiobiose | + |
| D-Turanose | + |
| D-Lyxose | − |
| D-Tagatose | + |
| D-Fucose | − |
| L-Fucose | − |
| D-Arabitol | − |
| L-Arabitol | − |
| Potassium gluconate | + |
| Potassium 2-ketogluconate | − |
| Potassium 5-ketogluconate | − |

Example 4 Preparation of PS128 for Animal Treatment

PS128 was inoculated in culture medium (10% skim milk, 1% yeast powder, 0.1% tween 80, and 2% glucose), cultured at 37° C. for 18 hrs and harvested by centrifugation. PS128 was embedded and lyophilized with protective agents (skim milk 1%, sugar 2%, oligofructose 2%, maltodextrin 3%, and glycerol 2%) and recipients to a final concentration of $5 \times 10^9$ colony formation unit (CFU) per gram powder. PS128 powder was stored at −20° C. and was dissolved into $10^{10}$ CFU/mL in saline solution before animal treatment.

Example 5 Improvement of MPTP-Induced Motor Deficits and Protection of Dopaminergic System in Mice's Brain by *Lactobacillus plantarum* Subsp. *Plantarum* PS128

(1) Animals and Housing

Six to eight-week-old Male C57BL/6J mice (20 to 22 g) were purchased from National Labtoratory Animal Center (Taipei, Taiwan). The mice were housed under constant temperature and humidity with 12 hours light-dark cycles, and were given free access to food and water. All animal experimental procedures were reviewed and approved by the Animal Management Committee, National Yang-Ming University.

(2) Experiment Procedure

Mice were oral administration with PS128 ($10^9$ CFU/mL per day) or saline (0.2 mL per day) respectively for 28 days. Mice were under intraperitoneal injection of MPTP (300 mg/kg) per day from 24th day to 28th day. Pole test, narrow beam test and rotarod test were demonstrated after the last MPTP treatment at 28th day. L-DOPA group was oral administration with 100 mg/kg L-DOPA+25 mg/kg benserazide & intraperitoneal injection of MPTP (300 mg/kg) per day from 24th day to 28th day and demonstrated as positive control. For further analysis, the mice were sacrificed in order to take out brain tissue, cecal component, and blood after all behavioral tests.

(3) Pole Test

Figure 2A:
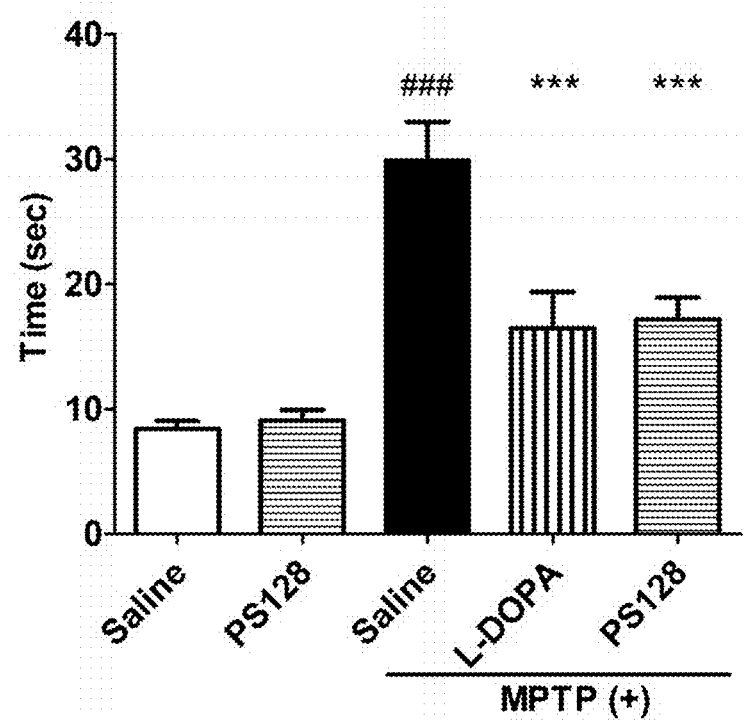
FIG. 2 A-C show the results of (A: pole test, B: narrow beam test, and C: rotarod test after MPTP intraperitoneal injection. (n≥6, *$p<0.05$, $p<0.01$, *$p<0.001$).

Pole test is a useful method for evaluating the mouse movement disorder. Referring to FIG. 2A, the mouse was placed head-upward on the top of a vertical rough-surfaced pole (diameter 1 cm; height 50 cm) and the time until it descended to the floor was recorded with a maximum duration of 120 s. Even if the mouse descended part way and fell the rest of the way, the behavior was scored until it reached to the floor. When the mouse was not able to turn downward and instead dropped from the pole, the locomotion activity time ($T_{LA}$) was taken as 120 s (default value) because of the maximal severity.

(4) Narrow Beam Test

Figure 2B:
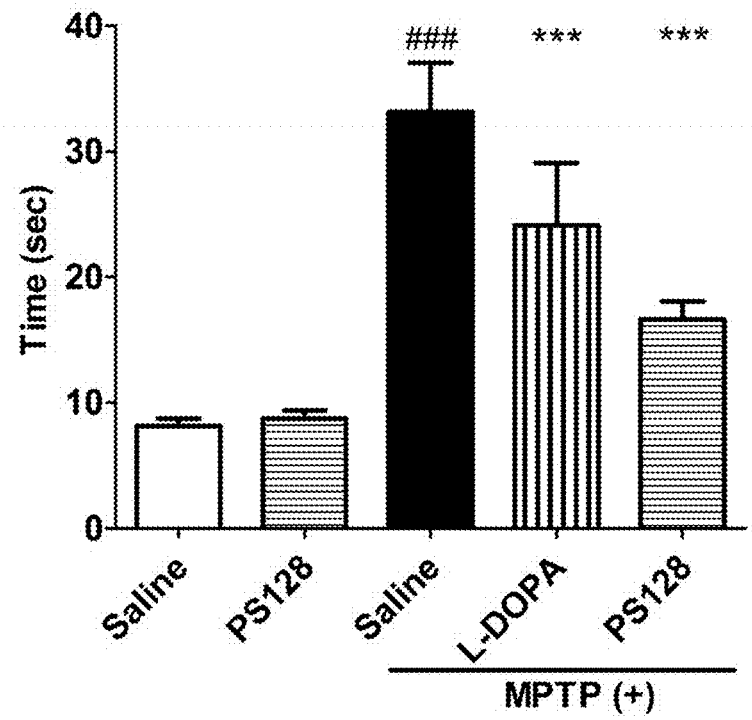

Narrow beam test is a useful method for evaluating the mouse motor coordination and balance. Referring to FIG. 2B, the beam apparatus consists of 50 cm beams with a flat surface of 0.8 cm width resting 50 cm above the table top on two poles. A black box is placed at the end of the beam as the finish point. Feeds from home cages are placed in the black box to attract the mouse to the finish point. On training days, mouse was placed in the black box in 5 minutes for environmental familiarization. After that, each mouse crossed the 5 cm beam 3 times followed by 15 cm, 30 cm and 50 cm beam training. On the test day, each mouse was demonstrated beam test 3 times and the crossing time was recorded.

(5) Rotarod Test

Figure 2C:
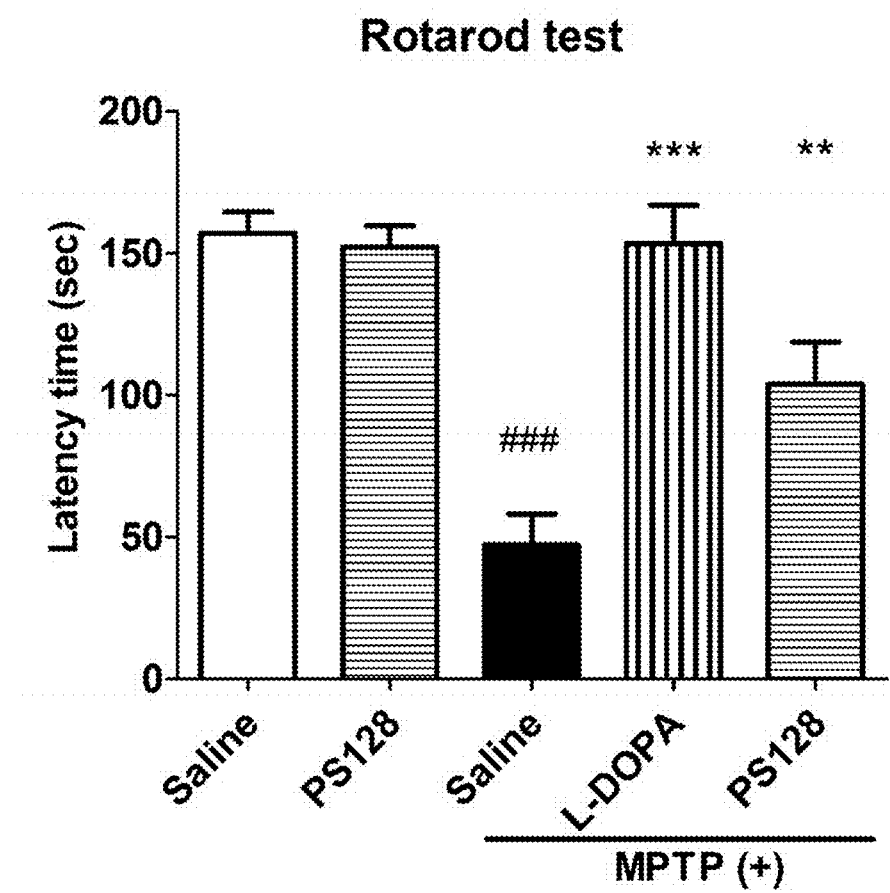

The rotarod test is widely used to evaluate the motor coordination of rodents. Referring to FIG. 2C, a rotarod machine with drums, automatic timers and falling sensors were used. The mice were under pre-rotarod training (30 rpm rotary speed for 180 seconds) for 3 days before MPTP injection. On the test day, each mouse was demonstrated rotarod test (30 rpm rotary speed for 180 seconds) 3 times contiguously (1 min interval between each test) and the remaining time was recorded.

(6) Quantification of Tyrosine Hydroxylase-Positive Dopaminergic Cells by Immunohistochemistry Mouse were anesthetized with sodium pentobarbital (50 mg/kg) and perfused transcardially with phosphate buffered saline (PBS) followed by 4% paraformaldehyde in PBS. Brains were immediately removed, placed into the same fixative overnight, and then transferred to a 30% sucrose solution at 4° C. before sectioning at 40 µm on a cryostat.

Sections were washed 3 times by wash buffer (0.1% triton X100 and 0.01% sodium azide in PBS) and then were incubated in block buffer for 1 hour with shaking under room temperature. After blocking procedure, sections were incubated with the primary antibody (anti-tyrosine hydroxylase, 1:300, Millipore) and Hoechst 33258 (1:2000, LIFE TECHNOLOGIES) in PBST (0.3% triton X100, 0.01% BSA, 0.01% Sodium azide and 3% donkey serum in PBS) overnight at 4° C. After three washes in wash buffer with shaking, sections were incubated with the secondary antibody (FITC-conjugated Affinipure Donkey anti-mouse IgG (H+L), 1:300, Jackson ImmunoResearch) and Hoechst in PBST for 2 hours with shaking under room temperature. Sections were then washed in wash buffer three times and sealed by mounting coverslip with mounting medium.

Figure 3A:
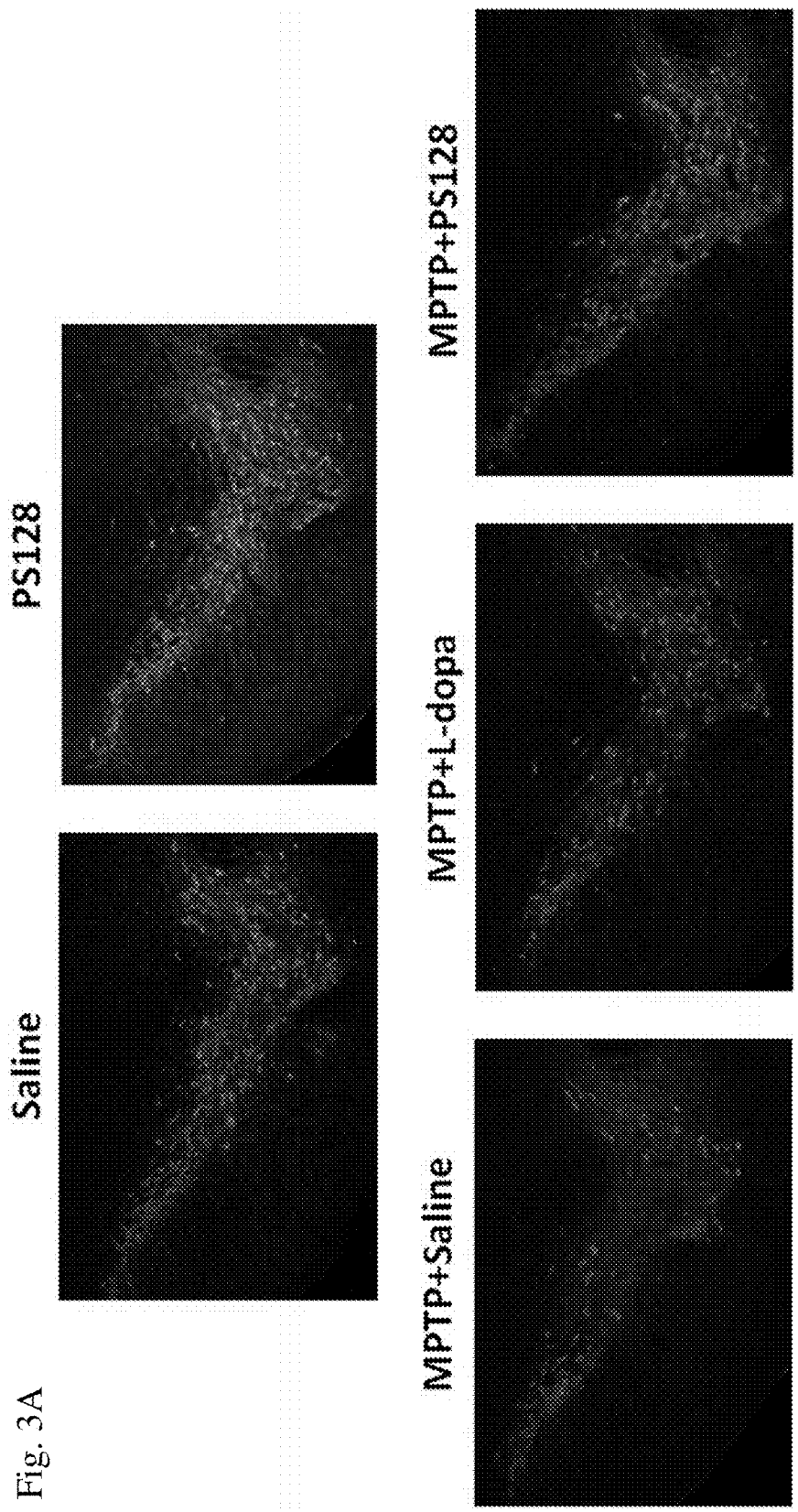
FIG. 3 A-B show the immunofluorescence staining pictures of TH positive cells in substantia nigra area (FIG. 3A) and quantification (FIG. 3B).
Figure 3B:
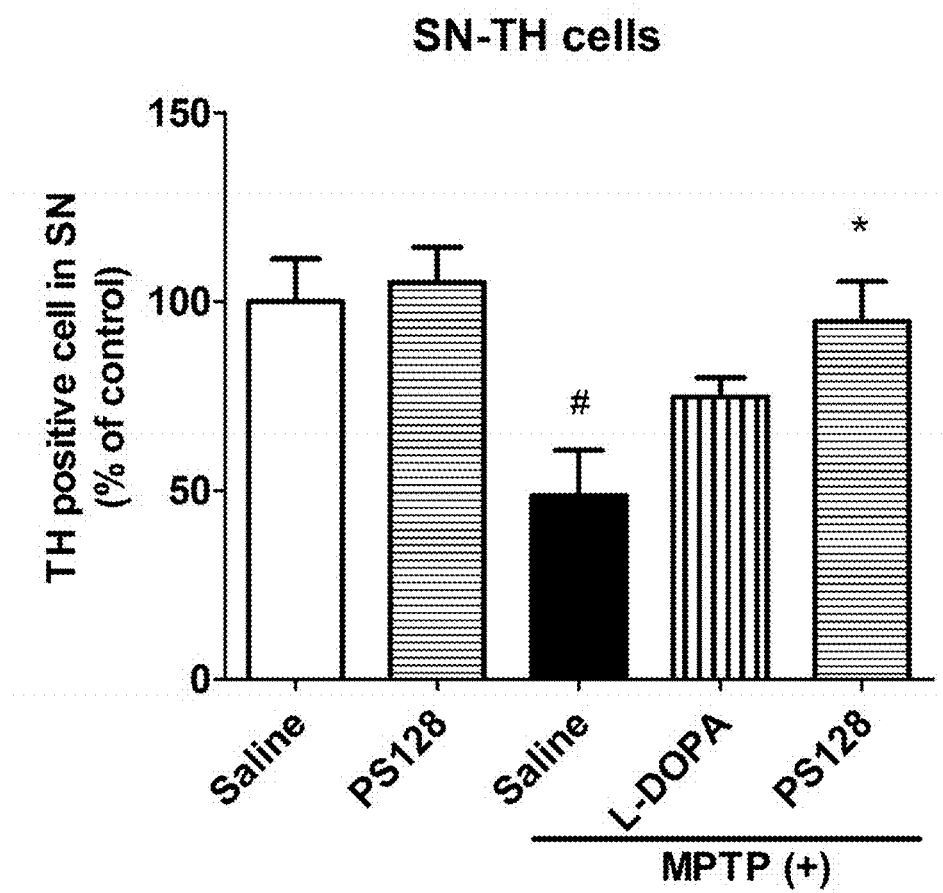

Immunostained sections were imaged by confocal microscopy leiss zsm700. The TH positive cell number was determined on alternate sections from Bregma −2.92 to −3.8 mm with MetaMorph software using the Multi Wavelength Cell Scoring application. Referring to FIG. 3A-B, the immunofluorescence staining pictures of TH positive cells in substantia nigra area (FIG. 3A) and quantification (FIG. 3B) were showed in percentage of saline control group.

Example 6 Amelioration of DOI-Induced Back Muscle Contraction and Abnormal Dopamine Signaling Pathway in Rat's Brain by *Lactobacillus plantarum* Subsp. *Plantarum* PS128

(1) Animals and Housing

Six to eight-week-old Male Wistar rats (220 to 330 g) were purchased from BioLASCO Taiwan Co., Ltd (Taipei, Taiwan). The rats were housed under constant temperature and humidity with 12 hours light-dark cycles, and were given free access to food and water. All animal experimental procedures were reviewed and approved by the Animal Management Committee, National Yang-Ming University.

(2) Experiment Procedure and Back Muscle Contraction (BMC) Numbers Counting

Figure 4:
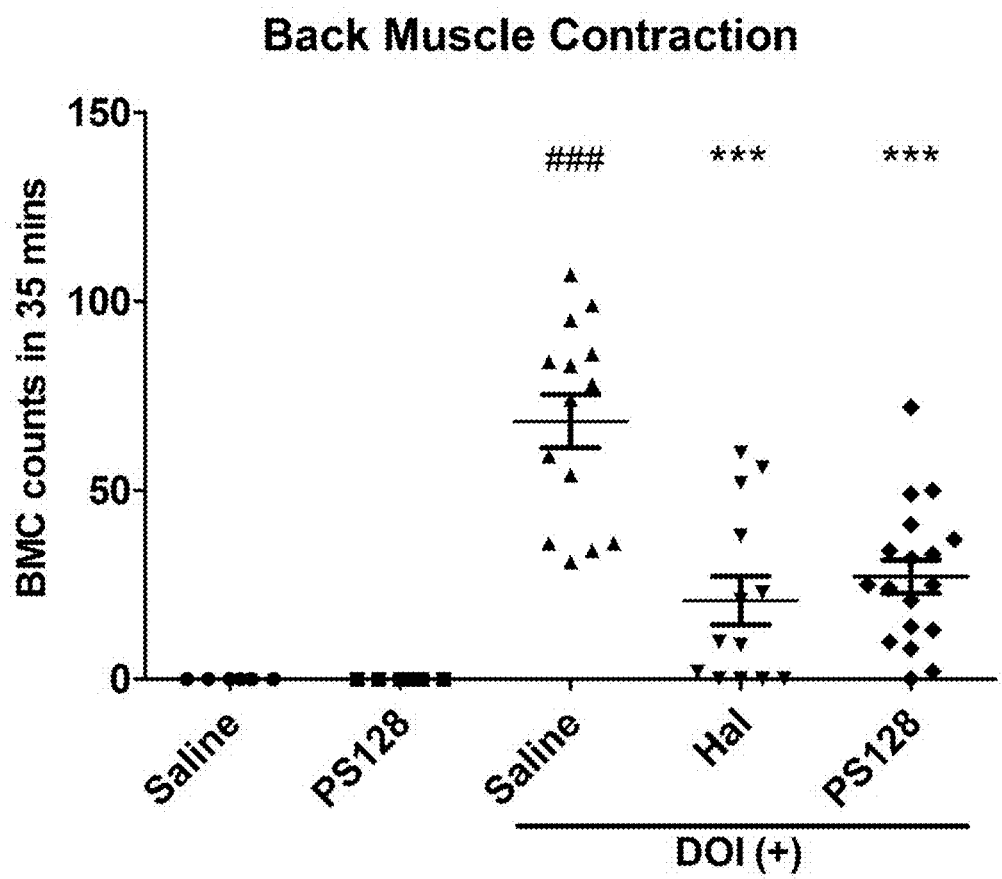
FIG. 4 shows the numbers of BMC counted immediately after the second treatment for a 35 mins period.

Rats were oral administration with PS128 ($10^{10}$ CFU/mL per day) or saline (1 mL per day) respectively for 15 days. Tics like behavior was established by two dose of 5-HT2A/C-receptor agonist 2,5-dimethoxy-4-iodoamphetamine (DOI), which produces robust frequencies of back muscle contraction (BMC). Rats were under intravenous injection of DOI (200 µg/kg) as a primary treatment on the 14th day and intraperitoneal injection of DOI (1 mg/kg) as secondary treatment on the 15th day. The numbers of BMC was counted immediately after the second treatment for a 35 mins period. Haloperidol (Hal) group was administration with dopamine antagonist haloperidol (1 mg/kg per day) respectively for 15 days and under same demonstration as a positive control. Referring to FIG. 4, BMC were counted only if a clear-cut powerful contraction sweeping from the back of the neck along the back to the tail was present (Fone et al., 1989). For further analysis, the rats were sacrificed in order to take out brain tissue, cecal component, and blood after BMC recording.

(3) Quantification of Monoamines and their Metabolites by High-Performance Liquid Chromatography-Electrochemical Detection (HPLC-ECD)

The HPLC-ECD system comprised a micropump (CMA-100, CMA, Stockholm, Sweden), an on-line injector (CMA-160), a Microtech LC-pump (Microtech Scientific, Sunnyvale, Calif., USA), a BAS-4C electrochemical detector (Bioanalytical Systems, Inc., West Lafeyette, Ind., USA), and a reversed-phase column (Kinetex C18, 2.6 um, 100×2.1 mm I.D.; Phenomenex, USA). The potential for the glassy carbon working electrode was set at +650 mV with respect to an Ag/AgCl reference electrode at room temperature (25° C.). The mobile phase containing 0.1 M $NaH_2PO_4$, 8% methanol, 0.74 mM 1-octanesulfonic acid (sodium salt), 0.03 mM ethylenediamine tetraacetic acid (EDTA), and 2 mM KCl was adjusted to pH 3.74 with $H_3PO_4$. The prefrontal cortex and striatum were lysed by sonication and centrifuged at 12,000×g for 10 min, and the resulting supernatants were filtered through a 0.22 mm polyvinylidene difluoride membrane (4 mm syringe filter; Millex-GV, Millipore, USA) before analysis. Diluted filtrates (20μL) were injected into the chromatographic system at a flow rate of 0.2 mL/min. Concentrations of dopamine (DA), dihydroxyphenylacetic acid (DOPAC), homovanillic acid (HVA), serotonin (5-HT), and 5-hydroxyindoleacetic acid (5-HIAA) in the samples were interpolated using standards (Sigma-Aldrich, St. Louis, Mo., USA) ranging from 1 to 100 ng/mL.

Figure 5A:
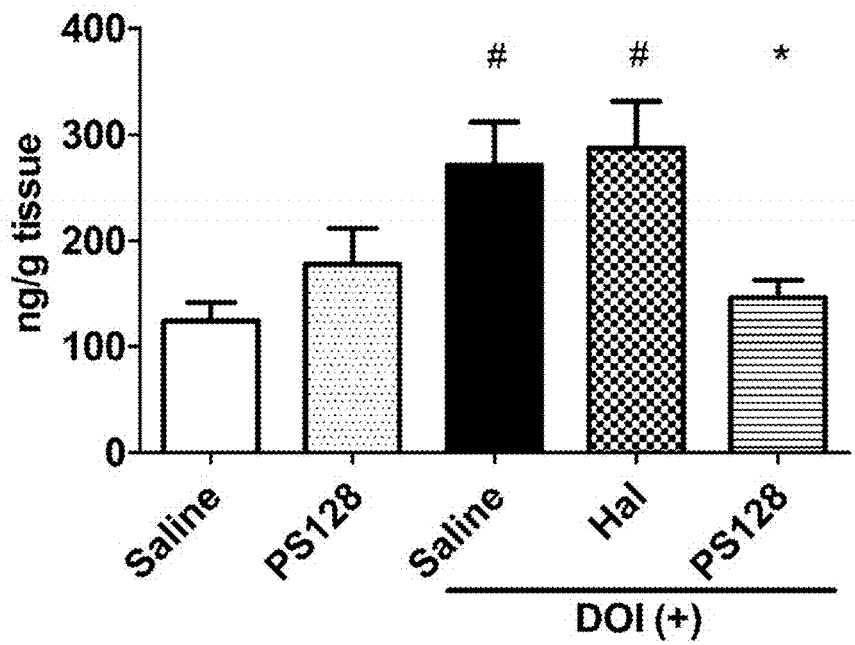
FIG. 5 A-D shows the total DA (A), DOPAC (B) and HVA (C) level in rat's prefrontal cortex and the neurotransmitter turnover ratio (DOPAC+HVA/DA (D)).
Figure 5B:
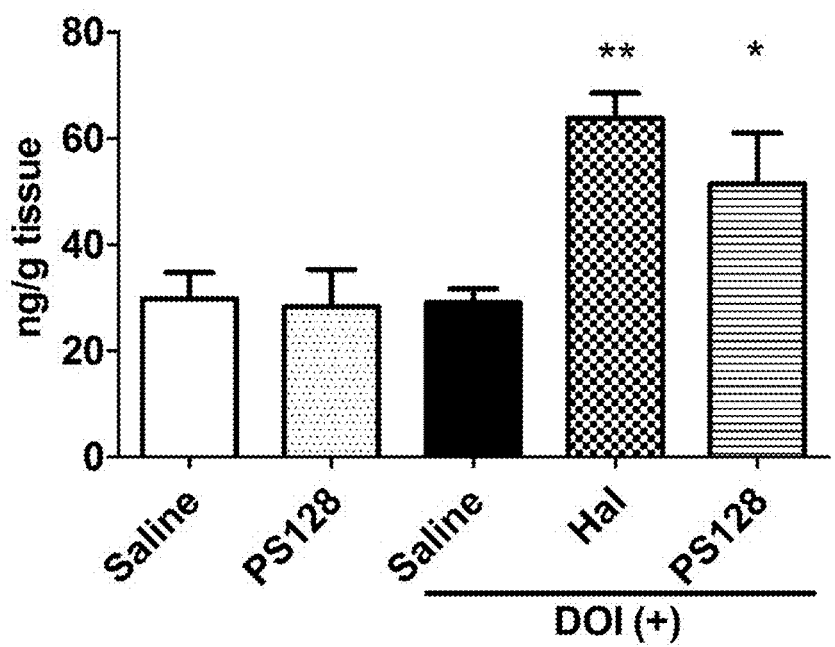
Figure 5C:
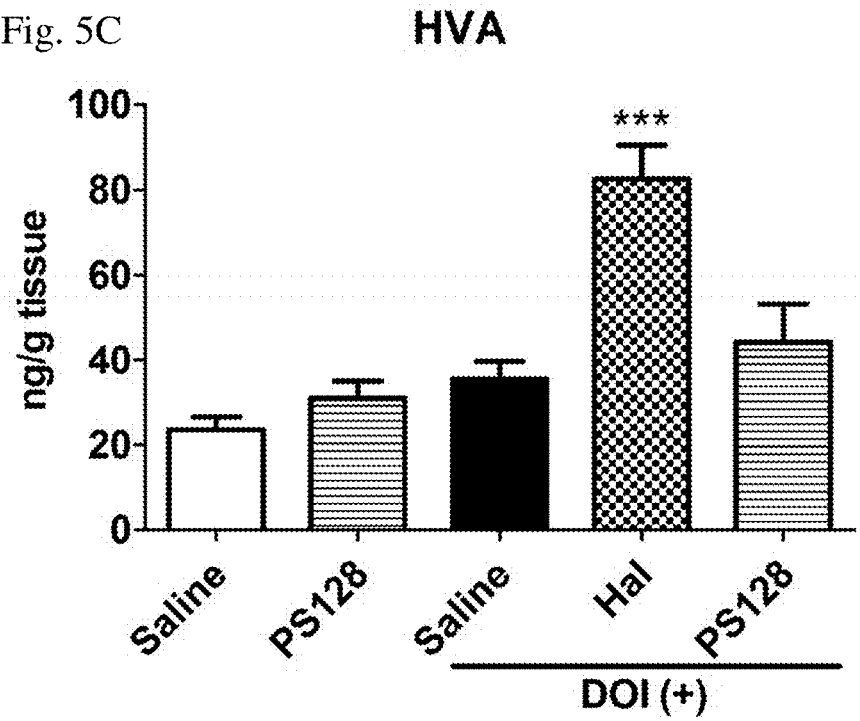
Figure 5D:
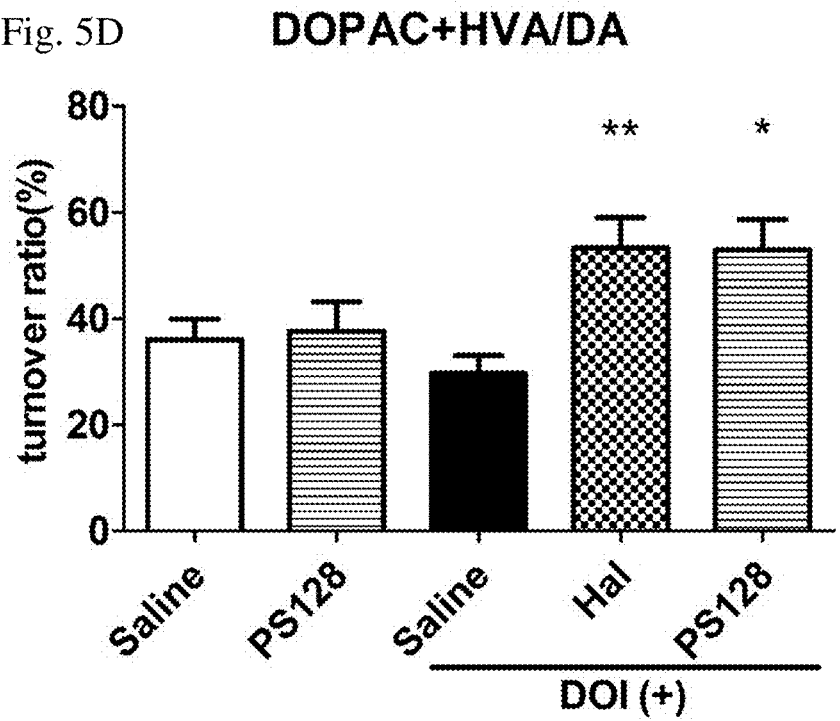

Referring to FIG. 5A-D, the total DA (FIG. 5A), DOPAC (FIG. 5B) and HVA (FIG. 5C) level in rat's prefrontal cortex were showed in ng per g tissue wet weight and the neurotransmitter turnover ratio (DOPAC+HVA/DA, FIG. 5D) was showed in percentage of total prefrontal cortical DA level. In FIG. 5A, the second PS128 bar refers to the administration of PS128 only (bacteria-onlycontrol group), which shows that no significant influence in DA total level; the fourth bar refers to the administration of haloperidol (Hal); and the last PS128 bar refers to the administration of PS128 to the mice receiving DOI. The third bar and the fifth bar show that the DOI significantly increases DA amount in the prefrontal cortex while PS128 administration modulates this tendency. FIG. 5B-5D show that the DA metabolic rate increases in the DOI-induced mice receiving PS128, so PS128 is able to modulate the abnormally increasing DA signal transmission in brain.

(4) Western Blotting

Figure 6A:
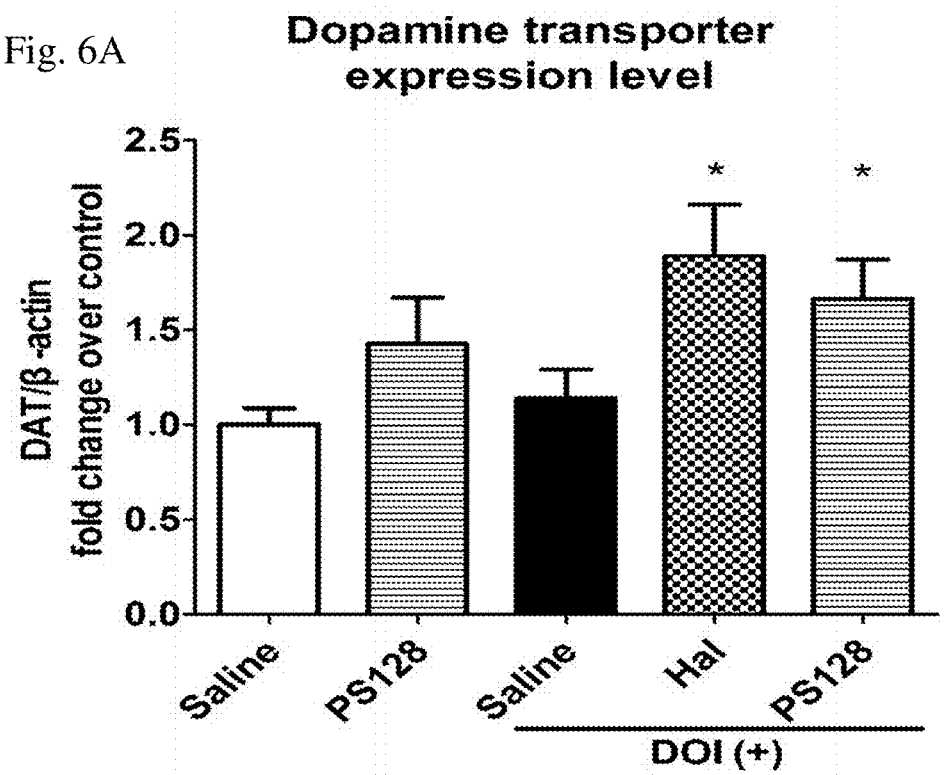
FIG. 6 A-C shows the rat's striatal DAT expression level (A), DARPP phosphorylation level (B) and ERK phosphorylation level (C).
Figure 6B:
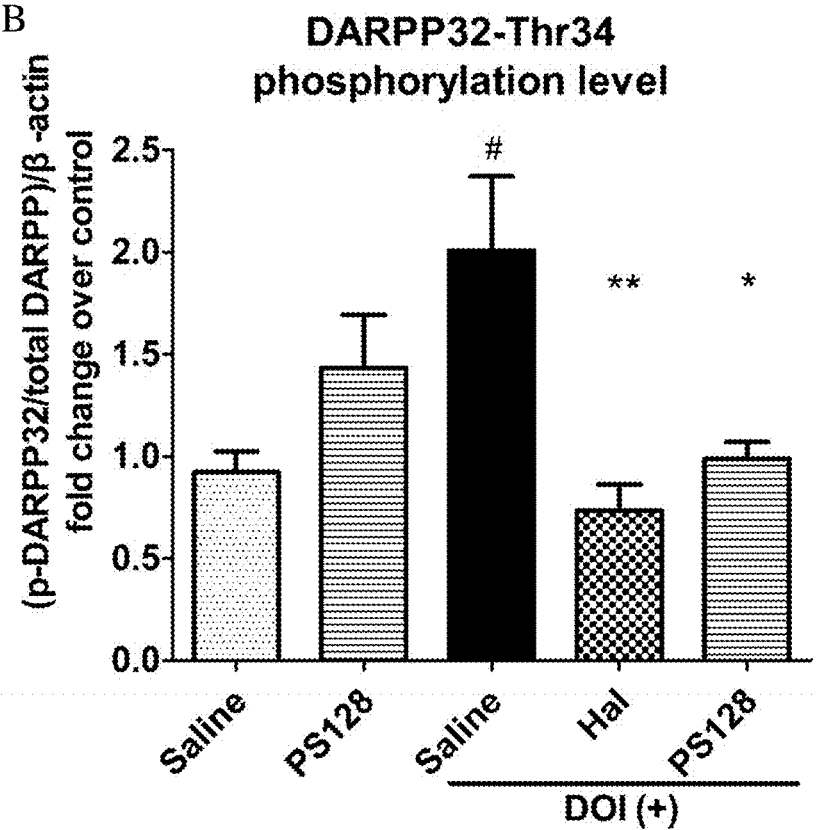
Figure 6C:
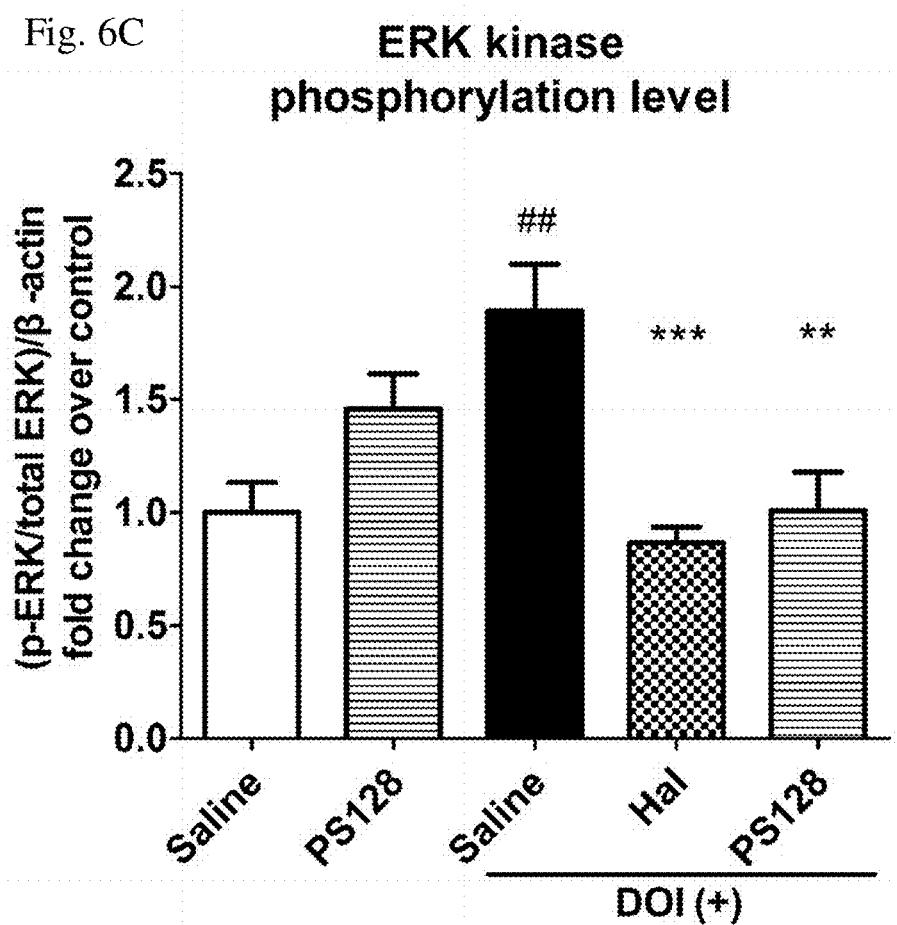
Figure 7A:
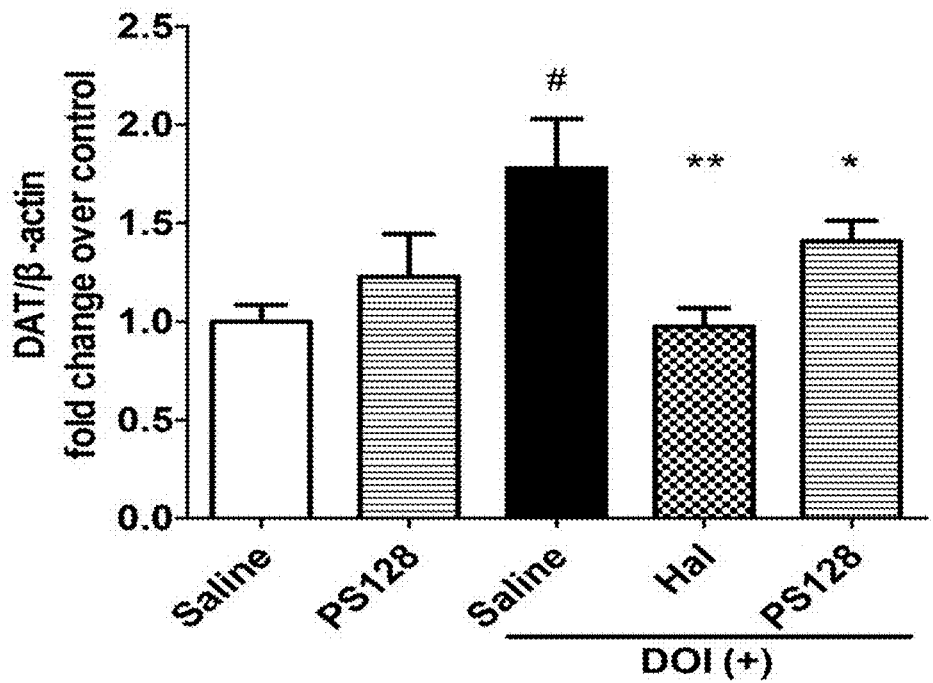
FIG. 7 A-C shows the rat's prefrontal cortical DAT expression level (A), DARPP phosphorylation level (B) and ERK phosphorylation level (C).
Figure 7B:
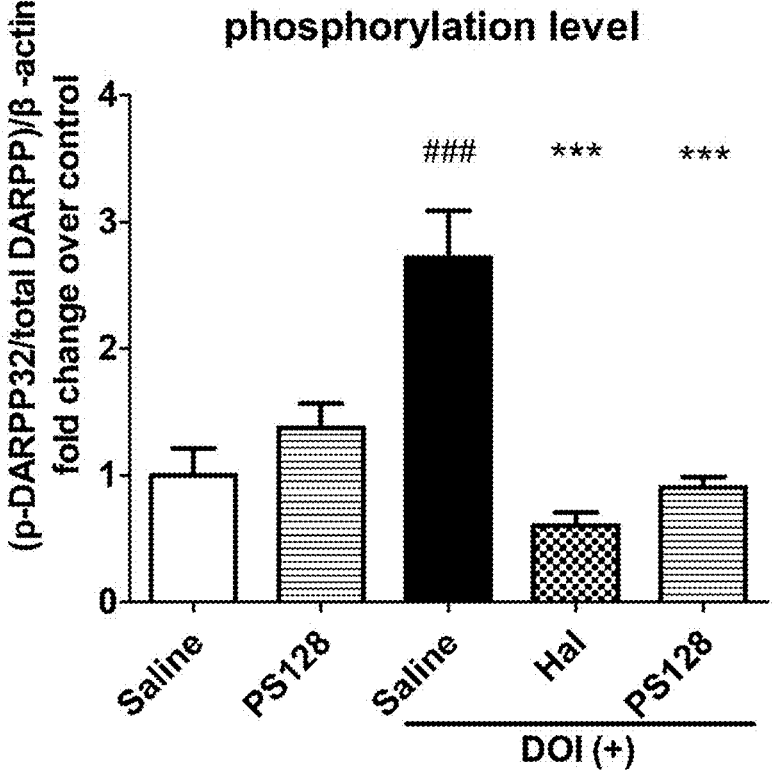

For confirming the effect of PS128 on DOI-induced abnormal dopamine signaling pathway by western blotting, total proteins in rat's prefrontal cortex and striatum. The extractions were fractionated on 10% polyacrylamide gels and then transfer to polyvinylidene difluoride membranes (Roche Ltd.) electrophoretically, followed by blockage for 1 hour with blocking buffer, TBST containing 5% Skim milk, and incubated with the primary antibody (anti-DAT 1:500; anti-pDARPP32 1:500; anti-pERK 1:1000; DARPP32 1:1000; ERK 1:1000; Santa Cruz Biotechnology, inc.) in blocking buffer overnight at 4° C. After twice washed with TBST, membrane was incubated with secondary antibody constructed with horseradish peroxidase in blocking buffer. The antibody-protein complex was visualized by Immobilon™ Western Chemiluminescent HRP Substrate (Millipore inc.) and detected by Luminescent Image Analyzer (FUJIFILM Holdings Corporation). Referring to FIG. 6A-C, the rat's striatal DAT expression level (FIG. 6A), DARPP phosphorylation level (FIG. 6B) & ERK phosphorylation level (FIG. 6C) was showed in fold change over control group. Referring to FIG. 7A-C, the rat's prefrontal cortical DAT expression level (FIG. 7A), DARPP phosphorylation level (FIG. 7B) & ERK phosphorylation level (FIG. 7C) was showed in fold change over control group.

What is claimed is:

1. A method of treating or preventing a basal ganglia disorder or a tic disorder in a subject, comprising administering an effective amount of cells of a *Lactobacillus plantarum* subsp. *plantarum* PS128, which is deposited under DSMZ Accession No. DSM 28632 to a subject.

2. The method of claim 1, wherein *Lactobacillus plantarum* subsp. *plantarum* PS128 has the 16S rDNA sequence as set forth in SEQ ID NO:3.

3. The method of claim 1, wherein the amount of PS128 cells for administration is at least $10^6$ cfu per day.

4. The method of claim 1, wherein the PS128 cells are in the form of whole bacteria.

5. The method of claim 1, wherein the PS128 cells are living or dead.

6. The method of claim 1, wherein the PS128 cells are partial cells of bacteria or a cell mixture of viable cells and dead partial or whole cells.

7. The method of claim 1, wherein the PS128 cells are prepared as a composition or mixture.

8. The method of claim 7, wherein the amount of PS128 cells for administration is $10^6$ to $10^{14}$ cfu per day.

9. The method of claim 7, wherein the composition or mixture is a nutritional or a pharmaceutical composition or mixture.

10. The method of claim 7, wherein the composition or mixture is a pharmaceutical product, a food product, a health food product, a nutritional supplement or medical food.

11. The method of claim 7, wherein the composition or mixture is prepared as a capsule, tablet, drink, powder or dairy product.

12. The method of claim 1, wherein the PS128 cells are orally administered.

13. The method of claim 1, wherein the basal ganglia disorder is hemiballismus, dystonia, psychostimulant addiction and Huntington's disease, Parkinson's disease, Tourette syndrome, or obsessive-compulsive disorder.

14. The method of claim 1, wherein the tic disorder is Tourette syndrome, DOI-induced tics-linked disorder, chronic motor disorder, or vocal tic disorder.

15. The method of claim 1, wherein the PS128 cells modulate dopamine neurotransmission in the basal ganglia.

16. The method of claim 15, wherein the neurotransmitter is selected from the group consisting of dopamine (DA), dihydroxyphenylacetic acid (DC), and homo-vanillic acid (HVA).

17. The method of claim 1, wherein the PS128 cells increase dopamine turnover rate in the prefrontal cortex.

* * * * *